United States Patent [19]

Zoltan et al.

[11] Patent Number: 4,790,305
[45] Date of Patent: Dec. 13, 1988

[54] MEDICATION DELIVERY SYSTEM

[75] Inventors: Bart J. Zoltan, Old Tappan, N.J.; Beth L. Laube; George K. Adams, III, both of Baltimore, Md.

[73] Assignee: The Johns Hopkins University, Baltimore, Md.

[21] Appl. No.: 877,331

[22] Filed: Jun. 23, 1986

[51] Int. Cl.[4] ..................... A61M 11/00; A61M 16/60
[52] U.S. Cl. ........................... 128/200.23; 128/203.28
[58] Field of Search ...................... 126/200.14, 200.18, 126/200.21, 200.22, 206.23, 203.25, 203.28, 203.29, 301.18, 205.13, 205.21, 716, 719, 720, 725, 727, 728, 730

[56] References Cited

U.S. PATENT DOCUMENTS 3,923,043 12/1975 Yanda ................................. 128/728
4,484,577 11/1984 Sackner at al. ................. 128/200.23

FOREIGN PATENT DOCUMENTS 773018 8/1934 France ............................ 128/203.28

OTHER PUBLICATIONS

Laros et al., "Absorption, Distribution and Excretion of the Tritium-Labelled $\beta_2$ Stimulator Fenoterol Hydrobromide Following Aerosol Administration and Instillation Into the Bronchial Tree", Respiration, vol. 131, p. 140 (1977).
Newman et al., "How Should a Pressurized $\beta$-Adrenergic Bronchodilator be Inhaled?," Eur. J. Respir. Dis., vol. 62, pp. 3-21, (1981).
Heimer et al., "The Effect of Sequential Inhalations of Metaproterenol Aerosol in Asthma", J. Allergy Clin. Immunol., vol. 66, No. 1, pp. 75-77, (1980).
Bell et al., "Variation in Delivery of Isoprenaline From Various Pressurized Inhalers" J. Pharm. Pharmac., vol. 25, Suppl., pp. 32-36, (1973).
Godden et al., "An objective Assessment of the Tube Spacer in Patients Unable to Use a Conventional Pressurized Aerosol Efficiently", Br. J. Dis. Chest, vol. 75, pp. 165-168, (1981).
Moven, "Drug Deposition of Pressurized Inhalation Aerosols", I. Influence of Actuator Tube Design, International Journal of Pharmaceutics, vol. 1, pp. 205-212, (1978).
"The Proper Use of Aerosol Bronchodilators", The Lancet, pp. 23-24, Jan. 3, 1981.
Gayrard et al., "Mauvaise Utilisation, des Aerosol-Doseurs par les Asthmatiques", Respiration, vol. 40, pp. 47-52, (1980).
Gumm et al., "Effect of an Extension Tube on the Bronchodilator Efficacy of Terbutaline Delivered from a Metered Dose Inhaler", Thorax, vol. 35, pp. 552-556, (1980).
Popa, "How to Inhale a Whiff of Pressurized Bronchodilator," Chest, vol. 76, pp. 496-498, (1979).
Freigang, "New Method of Beclomethasone Aerosol Administration to Children Under 4 Years of Age", CMA Journal, vol. 117, pp. 1308-1309, Dec. 3, 1977.
Shim et al., "The Adequacy of Inhalation of Aerosol from Canister Nebulizers", The American Journal of Medicine, vol. 69, pp. 891-894 (1980).
Neuman et al., "Simple Instructions for Using Pressurized Aerosol Bronchodilators," Journal of the Royal Society of Medicine, vol 73, pp. 776-779, (1980).

(List continued on next page.)

Primary Examiner—Edward M. Coven
Assistant Examiner—K. M. Reichle
Attorney, Agent, or Firm—Cushman, Darby & Cushman

[57] ABSTRACT

Apparatus for use in inhaling pharmaceutical aerosols. The apparatus comprises a mouthpiece for supplying a pharmaceutical composition to the mouth of a patient, a rigid chamber for holding the aerosol prior to inhalation, the rigid chamber having orifices to limit the flow of air therethrough, and a collapsable chamber from which the patient inhales unmedicated air prior to inhaling the medicated air from the rigid chamber. The apparatus increases medication delivered to the small peripheral bronchi, while it limits deposition in the oropharynx. The patient is aided in inhaling a volume of unmedicated air, after which he automatically begins to receive the aerosolized medication with the inhaled air. The volumetric flow rate of the inhaled medication is kept below required limits for optimal dosing.

10 Claims, 5 Drawing Sheets

OTHER PUBLICATIONS

Ellul-Micallef et al., "Use of a Special Inhaler Attachment in Asthmatic Children", *Thorax*, vol. 35, pp. 620-623, (1980).

Neuman et al., "Deposition of Pressurised Aerosols in the Human Respiratory Tract", *Thorax*, vol. 36, pp. 52-55, (1981).

Poppius, "Inhalation of Terbutaline Spray Through an Extended Mouthpiece", *Respiration*, vol. 40, pp. 278-283, (1980).

Orehek et al., "Patient Error in Use of Bronchodilator Metered Aerosols", *British Medical Journal*, vol. 10, p. 76, (1976).

Graf et al., "Use of Pressurized Aerosols by Asthmatic Patients", *British Medical Journal*, vol. 10, pp. 76-77.

Woodcock, "Training Aid for Pressurized Inhalers", *Br. J. Dis. Chest*, vol. 74, pp. 395-397, (1980).

Lindgren et al., "Improved Aerosol Therapy of Asthma: Effect of Actuator Tube Size on Drug Availability," Eur. J. Respir. Dis., vol. 61, pp. 56-61, (1980).

Greico, "In Vivo Comparison of Triamcinolone and Beclomethasone Inhalation Delivery Systems", *Annals of Allergy*, vol. 45, pp. 231-234 (1980).

MEDICATION DELIVERY SYSTEM

FIELD OF THE INVENTION

This invention relates to a medication delivery system. More specifically, the invention is concerned with means for dispensing pharmaceuticals which are active when administered as aerosols. The invention is particularly useful for dispensing aerosol pharmaceuticals in the treatment of respiratory or pulmonary diseases although other uses are also contemplated.

BACKGROUND OF THE INVENTION

Certain medications, especially those intended for the treatment of acute and chronic respiratory disorders, are most effective when inhaled directly into the lungs. Numerous pharmaceutical products are available for use as aerosols administered from metered dose inhalers. For example, bronchodilators are used in the treatment of bronchospasm and mucosal edema. Antibiotic aerosols are used to treat bronchial infections, anti-inflammatory steroids are used in the treatment of asthma, antifoaming agents are used in the treatment of fulminant pulmonary edema, and cromolyn sodium is used to control allergic asthma.

There is extensive literature indicating the successes of aerosol therapies, as well as the difficulties of using the aerosols properly. See, for example, *Respiratory Infection: Diagnosis and Management,* J. E. Pennington ed. Raven Press, N.Y.; *Chest* 1981, 80:911–915; *Arch. Int. Med.* 1973, 131:88–91.

Notwithstanding the very considerable development of aerosols and methods of using the same, there is still room for improvement in the administration of pharmaceutical aerosols. This is true not only in the case of drugs which are conventionally used in aerosol form but also to permit treatments which currently have to be conducted in some other less desirable fashion. Thus, improved and specific delivery of drugs in aerosol form to the lungs offers the possibility of therapies which are now considered impractical with other devices currently available. Polypeptides are made up of amino acid sequences, and include large molecules like insulin, and all of the products of recombinant DNA (rDNA) techniques. They are broken down in the digestive tract, and therefore the intact polypeptide molecule is not absorbed into the bloodstream. As a consequence, the only practical way to administer drugs of this type is by injection although nasal routes of administration have been suggested. It would be advantageous to provide an effective way of administering such a drug by way of the lungs.

Tissue plasminogen activator (t-PA) appears to be successful in halting damage done to cardiac muscle during myocardial infarction. There could be an advantage to be being able to carry this drug as an inhalant, and administering it without the need to wait for a physician or paramedic.

Delivery of therapy in pneumonia directly to the lung also has merit. Ordinarily, the concentration of antibiotic in the sputum is only two to three percent of the concentration in blood. In pneumonia or in cystic fibrosis, antibiotic concentration in the sputum is believed to be the determining factor for efficacy of the therapy.

A major problem of aerosol therapy is to deposit the aerosol on the walls of small bronchi and bronchioles, where the action of the medication is most often required. Less then ten percent of the medication delivered by standard metered dose inhalers reaches the typical patient's lungs. Most of the ninety percent of the medication which does not penetrate the target area is deposited in the mouth, throat, and trachea, and is eventually ingested. A small fraction of the aerosol is exhaled. The medication which deposits in the mouth and throat may lead to dysphonia and/or oral and laryngeal candidasis while the medication which is ingested serves no medical purpose to the patient, and is responsible only for undesirable side effects.

There are several problems to consider in the proper delivery of inhaled drugs to the lungs:

(1) The aerosol should consist of small particles, less than 5 microns, since larger particles cannot negotiate the sharp turns to the lung and are deposited in the oropharynx due to inertial effects. In order to minimize mouth deposition further it has been shown that the volumetric flow rate of the inhaled aerosol should be below 30 liters per minute.

(2) Metered dose inhalers deliver aerosol at a very high velocity directly into the patient's mouth where most of the medication impacts and is deposited in the mouth. This high initial velocity of the aerosol is a major factor in the ineffectiveness of many inhaler systems.

(3) Particles that persist in the airstream beyond the oropharynx may deposit on the larynx and on the walls of the trachea and of the large bronchi due to turbulence if the patient inhales at a volumetric flow rate above 30 liters per minute.

(4) In pulmonary physiology, the term "vital capacity" is the volume of air a patient can voluntarily exhale after having inhaled to total lung capacity. The vital capacity can vary from 2 to 5 liters depending on fitness, disease, gender, and age. It has been shown that in order to obtain maximum benefit from inhaled aerosols, the medication should be inspired after the patient has inhaled to at least 20 percent of his vital capacity. There is lack of agreement on the precise optimum, with the extremes being from 20 percent to 80 percent of vital capacity. In any case, after the medication has been inhaled, it is best to continue inhaling to total lung capacity, followed by holding of the breath for four to ten seconds, if possible.

(5) The device should limit the volumetric flow rate of the medication and aerosol as they enter the mouth, and should also allow the medication to be inhaled at a predetermined point in the respiratory cycle. Additionally the device should make it possible to inhale to total lung capacity. Furthermore, the size of the device should allow the user to carry the device around without too much inconvenience, and the cost to the patient should also obviously be low.

The medication delivery system of the present invention meets all of the above criteria. It is based on work done to image the deposition of aerosol medications in the human lung. This work utilized aerosol medications tagged with radioactive emitters, and used some of the currently available inhalation aids which are described hereinafter.

PRIOR ART

Several pharmaceutical manufacturers have included or sold separately with their aerosol products, what are referred to variously as "spacers", "inhalers", "drug inhalers", "oral adapters", "space-inhalers", and "spray inhalers" to be used in conjunction with their products.

Of the presently known prior art, only one device (namely that known as InspirEase TM from Key Pharmaceuticals) addresses the known problems of aerosol inhalation. This device is essentially a collapsible bag into which the medication is metered, and from which the patient inhales. The mouthpiece of the device contains a whistle which is silent at low flow rates, but sounds when the patient is inhaling too rapidly.

Laboratory equipment has also been described allowing inspired air to be measured using a pneumotachygraph. The flow rate signal is integrated by a computer and an aerosol canister containing the medication is actuated automatically at a predetermined lung volume using a solenoid mounted on top of the aerosol actuator (see papers by Newman et al, *Thorax* 1981 36:52–55; *Thorax* 1980, 35:234; *Eur J. Respir. Dis* 1981, 62, 3–21; *Am Rev. Respir Dis.* 1981, 124:317–320). While this system is suitable for experimental studies, it is impractical for use in routine therapy because of size and cost.

BRIEF DESCRIPTION OF THE INVENTION

The present invention overcomes disadvantages associated with prior art attempts, and provides the patient and his physician with a practical means of taking aerosol medication in an optimal manner at low cost. This is achieved by metering the aerosol medication into a first rigid chamber, from which first chamber the patient inhales the medication. The first chamber is of a flow-through design, so that the patient may continue to inhale from the first chamber even after the initial volume has been inspired.

Throughout this specification, the term "rigid chamber" refers to the chamber while in use. It is recognized that for the sake of portability it may be desirable to fold or collapse the device of the invention into a small space. Thus the term "rigid" is meant to be applied in the same way that an umbrella may be described as rigid when in use, although it may be collapsible and stored in a closed configuration and opened or extended into rigid form prior to use.

According to the invention, the volumetric flow rate is limited by the use of orifices in the first chamber. The orifices are nominally sized for the typical frail patient, with provisions for closing one or several orifices if the physician or the patient feels that the nominal setting is inappropriate for a specific patient.

Another feature of the invention is to make it easy for the patient to inhale the medication at the proper point in his respiratory cycle. Thus, besides the first rigid chamber referred to above, the invention utilizes a collapsible second chamber with an adjustable volume. This second chamber can be adjusted at the discretion of the physician to provide a volume equal to the volume of air to be inhaled by the patient before the medication is to be inhaled. This can be adjusted depending on the condition of the patient and on the prescription of the physician.

In use, the aerosol medication is metered into the rigid first chamber. The patient inhales through a single mouthpiece. Initially all of the air is inhaled from the collapsible second chamber. When this second chamber has been exhausted, the patient automatically begins to inhale from the rigid first chamber containing the medication. The volumetric flow rate is limited to, for example, 30 liters per minute, by the orifices provided in the first rigid chamber as referred to above. The patient continues to inhale until he reaches his maximum capacity, at which time he attempts to hold his breath for the time recommended by this physician.

Broadly defined, the delivery device of the invention comprises a mouthpiece having a medication inhalation end and another end; means for connecting a medication container to the mouthpiece intermediate the ends; first chamber means fixed to the mouthpiece at the other end for mixing medication from the container with air before inhalation thereof; and further chamber means fixed to the mouthpiece for supplying a variable volume of air to the inhalation end for inhalation before the mixture is inhaled. The device also includes orifice means to limit the volumetric flow rate, the rate at which the patient is able to inhale the aerosolized medication. The air to medication ratio can be varied as desired so long as the medication reaches the lungs.

In a more specific description, the present device comprises: a first rigid chamber; a second collapsible chamber; and a mouthpiece which has a first end and a second end, the mouthpiece also having a first passageway extending lengthwise therethrough from the first end to the second end so that medication and air fed into the second end can be inhaled at the first end, the first end being shaped accordingly to accommodate the human mouth for inhalation purposes. The mouthpiece further includes a second passageway transverse to the first passageway and positioned between the first end and the second end in open communication with the first passageway. The mouthpiece further includes means for connecting to a medication container, and passage means for directing medication from the container out the second end of the mouthpiece for discharge into the first rigid chamber. This rigid chamber has first and second end walls, the first end wall having an opening which is pneumatically connected to the first passageway of the mouthpiece at the second end thereof while the second end wall of the first chamber has one or more orifices for the purpose of limiting the volumetric flow of air through the chamber. The device allows the user to meter medication into the first rigid chamber, and to inhale through the mouthpiece, automatically inhaling the non-medicated contents of the second collapsible chamber before inhaling a mixture of air and medication from the rigid first chamber.

The medication container may comprise a pressurized aerosol, a spray dispenser or any other convenient means for dispensing medication, preferably in a metered or dosage amount.

BRIEF DESCRIPTION OF THE DRAWINGS

The invention is described in more detail by reference to the accompanying drawings wherein.

DETAILED DESCRIPTION OF THE INVENTION

Figure 4:
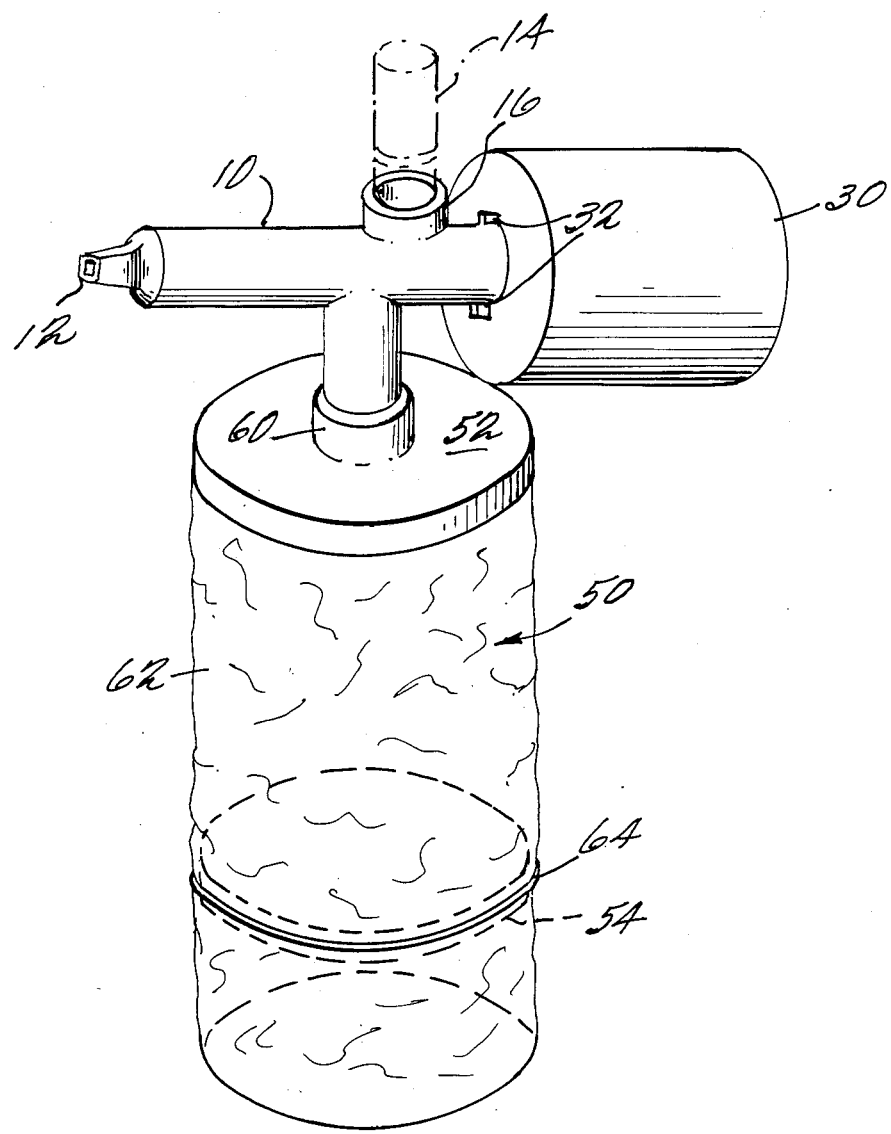
FIG. 4 is a perspective view of the assembled device including the mouthpiece, rigid chamber and collapsible chamber.

Referring more specifically to the drawings, the device of the invention, as shown in FIG. 4, comprises the mouthpiece member generally designated by the numeral (10), the first rigid container or chamber (30), the second flexible or collapsible container or chamber (50) and supply (14) of inhalant material to be administered. In use, a predetermined volume of air from the flexible or collapsible container (50) air is initially inhaled by drawing through the mouthpiece inlet end (12), followed by inhalation of a metered dose of material from (14), this material being first fed into (30) where it is held prior to inhalation by the patient, thereby eliminating the initial high velocity of the medication being directly discharged into the patient's mouth. Orifices in the rear end wall of chamber (30), as discussed later, limit the rate at which the patient can inhale the medication.

Figure 1:
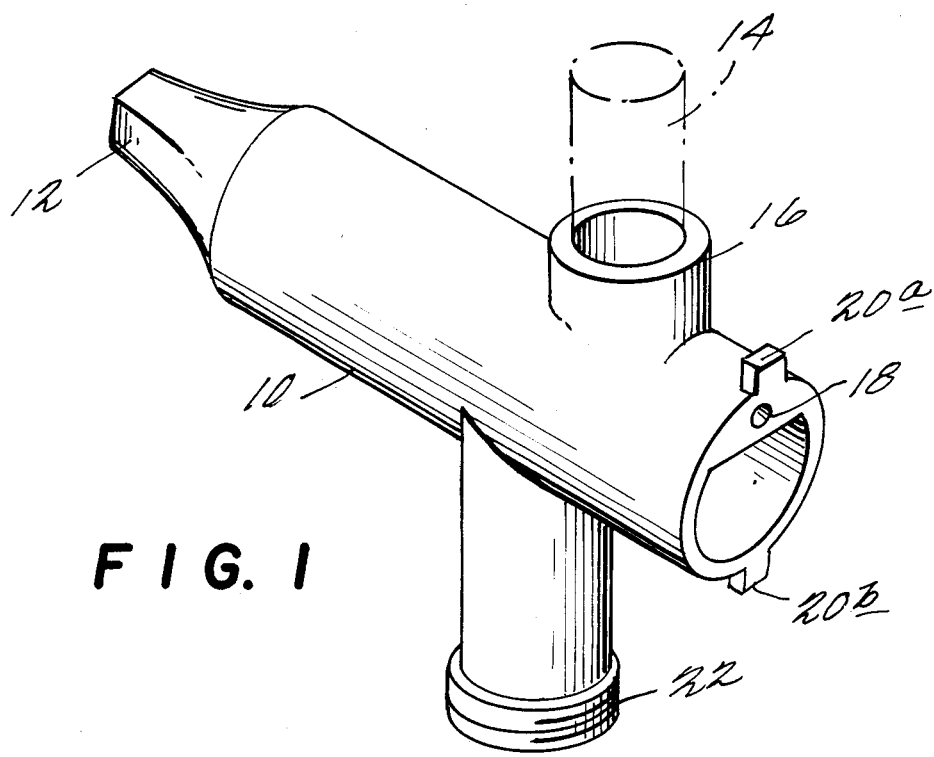
FIG. 1 is a perspective view of the mouthpiece of the present device.
Figure 1A:
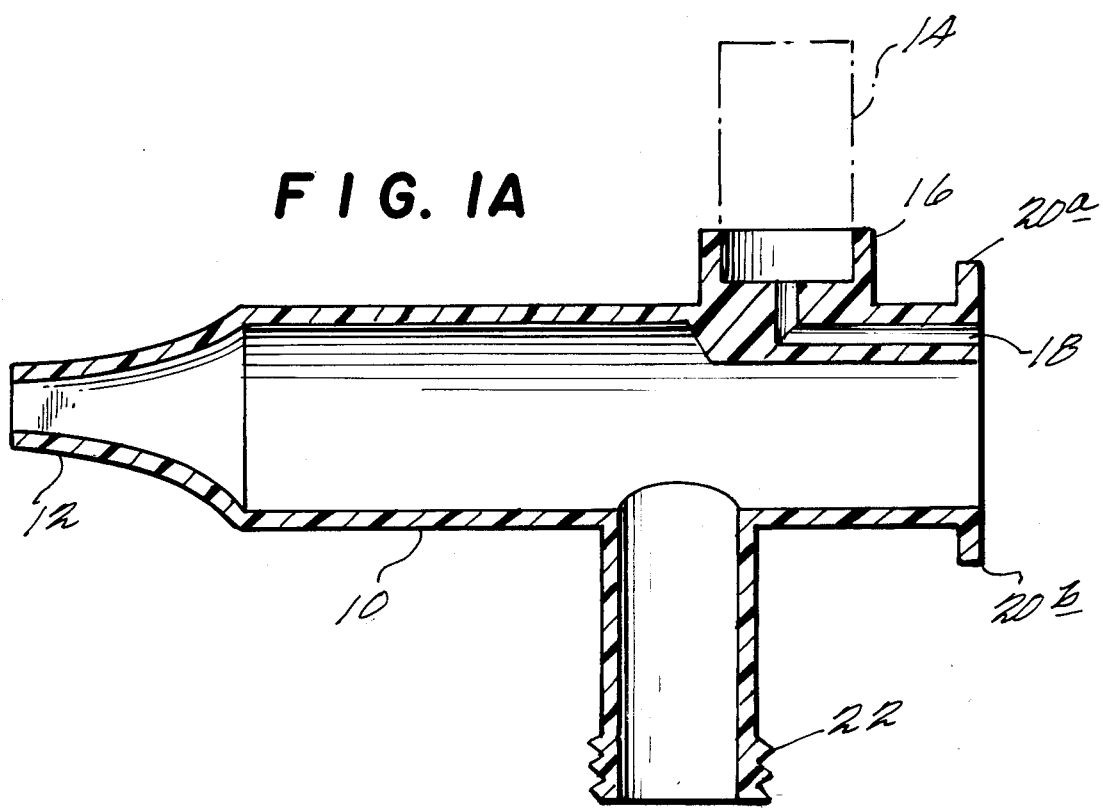
FIG. 1A is a cross-sectional view taken vertically through the mouthpiece of FIG. 1.

Turning now to FIGS. 1 and 1A, the mouthpiece (10) comprises a basically tubular member (8) which includes the lengthwise passageway (9), the latter communicating with the end (12) which is suitably shaped to be accommodated in the mouth of the patient. Member (8) also includes a socket (16) adapted to receive the container (14) with material to be inhaled. As noted earlier, container (14) may be a pressurized aerosol, a spray dispenser or the like. Preferably container (14) is any kind of conventional metered dose inhaler containing standard aerosol medication.

As shown in FIG. 1A, a passage (18) leads from the base of socket (16) to the rear end wall (20) of the mouthpiece. This passage directs the flow of aerosol material from the metered dose inhaler into the rigid chamber (30) when the inhaler (14) is pushed down or otherwise operated in pocket (16) to meter out a dose of medication.

The rear end wall (20) of mouthpiece (10) is also provided with lugs (20a) and (20b) to attach the mouthpiece to the rigid chamber (30) (as shown in FIG. 4).

Figure 3A:
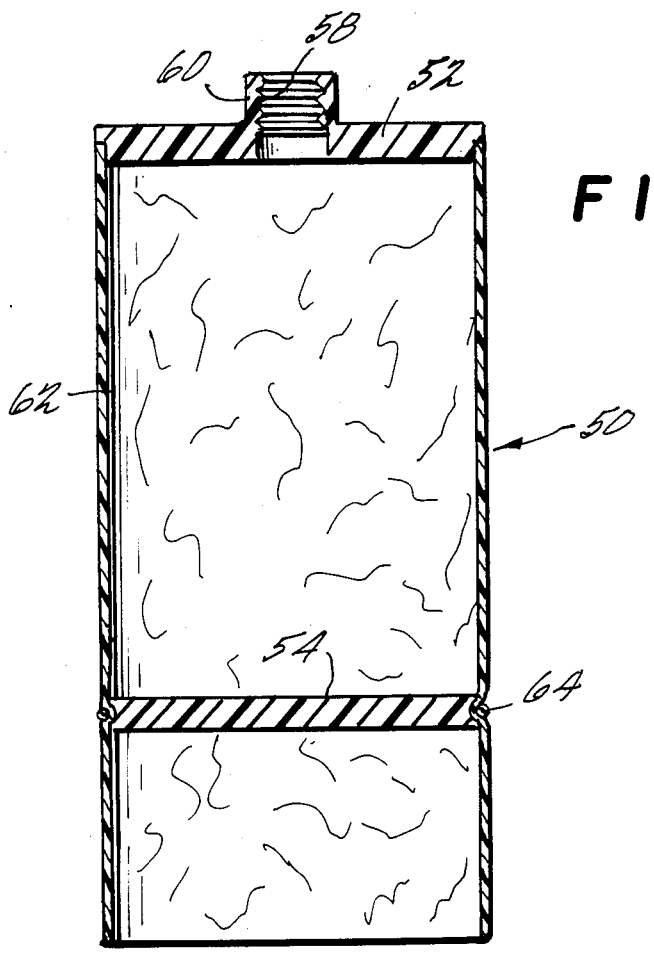
FIG. 3A is a vertical cross-sectional view of the second collapsible chamber including its supporting means.

Intermediate the inlet (12) and the socket (16) and on the opposite side of the body member from socket (16) is a tubular coupling member (22) which is conveniently threaded to receive a mating connection on the flexible container (50) shown in FIG. 3A.

Figure 2:
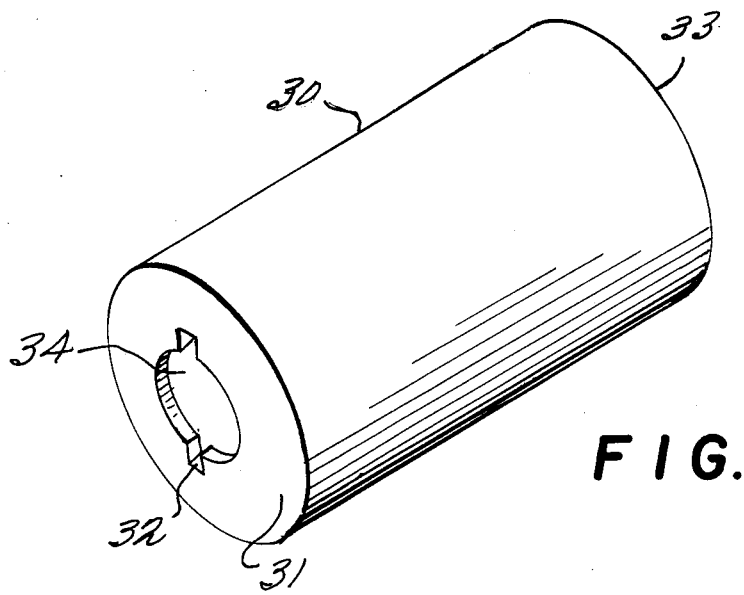
FIG. 2 is a perspective view of the rigid chamber.
Figure 2A:
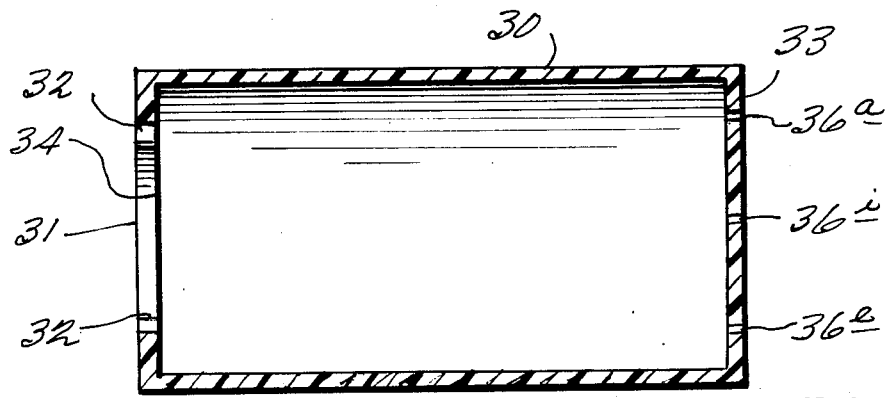
FIG. 2A is a vertical cross-sectional view of the rigid chamber.
Figure 2B:
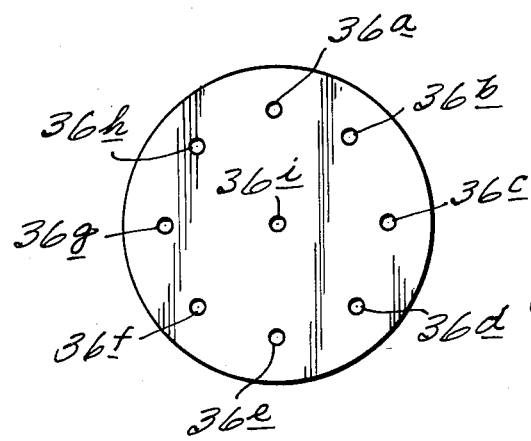
FIG. 2B is a rear end view of the rigid chamber showing the orifice therein.

FIG. 2 shows the rigid chamber (30) which is in the form of a hollow cylinder with front and rear end walls (31) and (33), respectively. End wall (31) is provided with a central opening (34) which is generally circular except for the opposed slots (32) which cooperate with lugs (20a) and (20b) of mouthpiece (10) to permit chamber (30) to be rigidly attached to the mouthpiece. It will be appreciated that this is done by pushing the lugs (20a) and (20b) through the slots (32) and then turning the chamber (30) or mouthpiece (10). The opening (34) communicates with passageway (18) and allows the contents of the metered dose inhaler (14) to be directed into chamber (30).

The rear end wall (33) of container (30) is provided with a plurality of small orifices (36a), (36b), (36c), (36d), (36e), (36f), (36g), (36h), and (36i). The number of these orifices can be varied as desired. In a preferred embodiment, nine orifices, each about 0.020 inches in diameter, are used but more or less than this number may be employed.

It will be appreciated that the orifices (36a)–(36i) permit air to be drawn into chamber (30) to be mixed with aerosol entering container (30) via passageway (18). Depending on the age and health of the patient, orifices may be advantageously covered, one at a time, until the volumetric flow rate for the patient is below 30 liters per minute. The covered orifices may be permanently or temporarily sealed as desired.

With reference to FIG. 3A, this shows the flexible, collapsible chamber (50) as comprising a generally flat, cylindrical support member (52) provided with a threaded coupling member (58) for mating attachment with means (22) of mouthpiece (10). Attached circumferentially to (52) is a flexible sleeve (62) which is, in the preferred embodiment, attached permanently to member (52) although the sleeve (62) may also be detachably fixed to member (52) if desired. When attached to the mouthpiece (10), the sleeve (62) simply hangs loosely. The sleeve may be made of any conveniently flexible plastic material or the like. A cylindrical plug (54), sized to loosely fit within sleeve (62), is also included to provide an adjustable closure for the sleeve. This plug is held firmly in position by a torus-shaped elastic (64) which serves to close the sleeve at the desired point by fitting tightly around the outside of the sleeve, the circumferential edge of the plug (54) being suitably grooved to receive the elastic with the sleeve held therebetween.

It will be appreciated that the volume of flexible sleeve (62) can be adjusted by moving plug (54) from its upper-most position, corresponding to a volume of zero, to the lowest position which, in a preferred embodiment, corresponds to, for example, two liters.

Figure 3B:
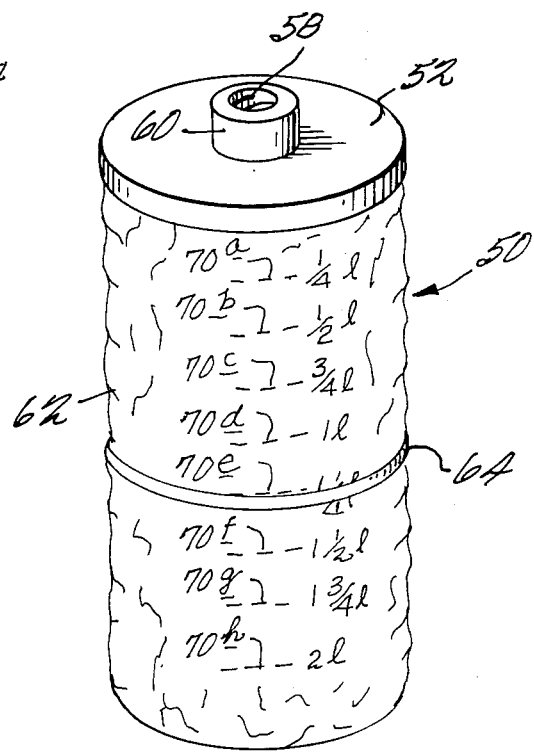
FIG. 3B is a perspective view of the collapsible chamber.

FIG. 3B is a view of the outer surface of the sleeve (62). As shown, the surface carries the indicia, (70a), (70b), (70c), (70d), (70e), (70f), (70g), and (70h) corresponding to volumes of ¼ litter, ½ liter, ¾ liter, 1 liter, 1 and ¼ liter, 1 and ½ liter, 1 and ¾ liters, and 2 liters. In this way, the volume of the collapsible chamber (50) can be varied as desired by approximately positioning the plug (54) and fixing it in place by the elastic means (64).

As will be appreciated, the delivery device is operated as follows:

The desired aerosol medication (14), preferably in standard metered container form, is positioned in recess (16). The elastic (64) and plug (54) are positioned to set the volume of the collapsible chamber (50) at the desired volume and the appropriate number of orifices in chamber (30) are opened or closed to give the required flow rate. The patient places the mouthpiece inlet (12) in his mouth and medication is metered out of the container (14), e.g. by pushing the container (14) down against the base of socket (16). The medication flows via passageway (18) into the rigid container (30) where it is mixed with air. The patient then inhales, receiving first the air from the collapsible chamber (50) and then a mixture of the metered medication and air from chamber (30). The patient then holds his breath for the required time.

It will be recognized that the present device may be made from a variety of different plastic materials or the equivalent to function as described.

The advantages of the invention are illustrated by the following tests, the results of which are shown in FIGS. 5A–5D:

Subjects were studied at the same time of day on two study days. On the first study day, subjects inhaled a 0.9% saline solution containing the radioisotope Tc-99m sulfur colloid ad libitum using a prior art device, a DeVilbiss #42 nebulizer. This nebulizer was connected to a 20 p.s.i. compressed air source through a nebulization dosimeter which controlled the duration of the compressed air pulse during aerosol generation. A manual trigger, controlled by the subject, was used to actuate the nebulizer air flow for a period of 0.6 seconds.

On the second study day, subjects inhaled the same radioaerosol using the #42 DeVilbiss nebulizer in conjunction with the subject invention. First there was manually triggered actuation of the nebulizer airflow, at which time radioaerosol was delivered to the rigid chamber of the present device. The volunteer then inhaled approximately 750 ml of room air from the collapsible chamber starting from residual volume. Residual volume is the air remaining in the lungs after exhalation. Once the collapsible chamber was empty, the subject inhaled the radioaerosol from the rigid chamber to total lung capacity, at which time the subject exhaled slowly with no breath holding.

Following the inhalation of the radioaerosol, the subject's left lateral skull and lungs were scanned for ten minutes each with a Technicare Model #110 gamma camera. Counts from the gamma camera were acquired in a 256 by 256 picture element (pixel) matrix and were processed for oropharyngeal and bronchopulmonary deposition in a 64 by 64 pixel matrix using an Informatek SIMIS 2 computer. Aerosol deposition in the regions of interest was expressed as a percent of total counts. The scan images were photographed directly from the computer display using a 35 mm camera.

Figure 5A:
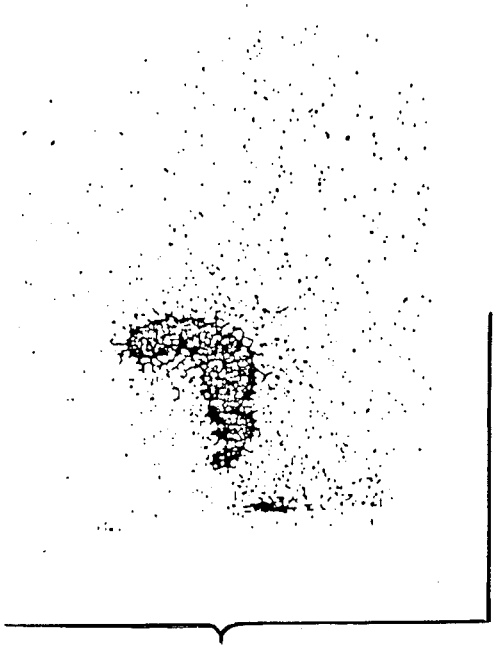
FIG. 5A is an image of the oropharyngeal deposition of radiolabelled inhalant inhaled using a prior art device, a DeVilbiss nebulizer.
Figure 5B:
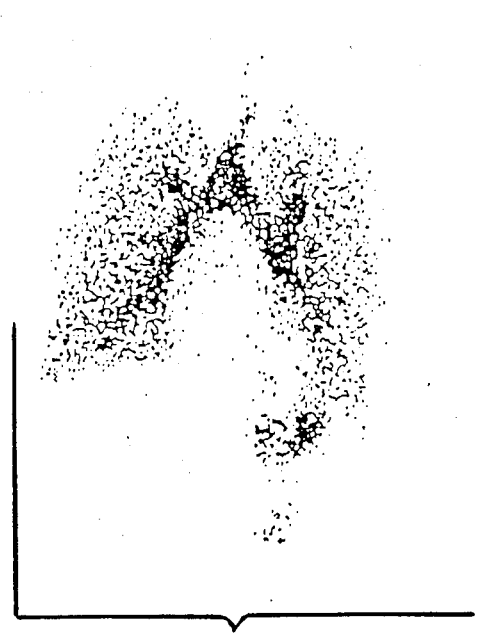
FIG. 5B is an image of the bronchopulmonary deposition of radiolabelled inhalant inhaled using a prior art device, a DeVilbiss nebulizer.

FIGS. 5A and 5B are gamma camera anterior images of the oropharyngeal deposition and bronchopulmonary deposition of the radiolabelled aerosol inhaled by one normal subject using the prior art device, a DeVilbiss #42 nebulizer. Oropharyngeal deposition was 28 percent of the total counts and bronchopulmonary deposition was 72 percent of total counts.

Figure 5C:
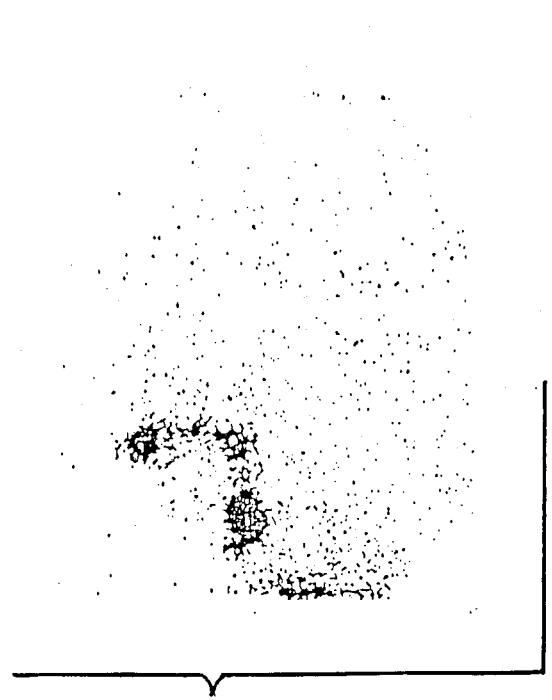
FIG. 5C is an image of the oropharyngeal deposition of radiolabelled inhalant inhaled using a DeVilbiss nebulizer in conjunction with the subject invention.
Figure 5D:
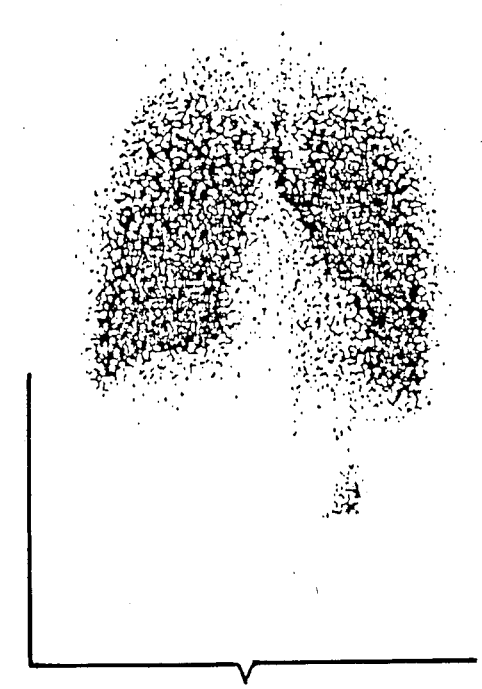
FIG. 5D is an image of the bronchopulmonary deposition of radiolabelled inhalant inhaled using a DeVilbiss nebulizer in conjunction with the subject invention.

FIGS. 5C and 5D are similar images, in the same subject, of the oropharyngeal deposition and bronchopulmonary deposition of the radiolabelled aerosol inhaled using the same nebulizer in conjunction with the subject invention. Oropharyngeal deposition was 6 percent of the total counts and bronchopulmonary deposition was 94 percent of total counts.

As will be evident, the invention increases the delivery of the aerosol to the bronchi while reducing deposition in the oropharynx.

As will be appreciated from the foregoing description, the present aerosol device is able to deliver drug specifically to the lungs. Accordingly, it offers a highly effective way of administering medication by aerosol to the lungs. Additionally the invention opens up a possible alternative for administering compounds which have previously been administrable only by injection. As noted earlier, the polypeptide products of recombinant DNA, for example, are degraded in the intestines and are normally given only by injection. The delivery of aerosolized drugs such as insulin in the manner proposed herein could result in the absorption of biologically-active drug across the mucosa of the human respiratory tract and thus avoid degradation in the intestines. The present aerosol delivery system accordingly, offers an option for effectively administering such drugs as insulin, tissue plasminogen activating factor and the like which are degraded in the intestines and normally only administered by injection.

It will be recognized that various modifications may be made in the invention as described above. Accordingly, the scope of the invention is defined in the following claims wherein:

We claim:

1. A device for delivery of aerosolized medication to a patient, said device comprising:
    a mouthpiece having an inhalation end and another end;
    means for connecting a medication container to said mouthpiece intermediate said ends;
    first chamber means fixed to said mouthpiece at said other end for holding the aerosolized medication before inhalation thereof; and
    further chamber means fixed to said mouthpiece for supplying a variable volume of air to said inhalation end before the aerosolized medication is inhaled.

2. The device of claim 1 including means for varying the resistance of said first chamber means to the flow of air therethrough.

3. The device of claim 2 wherein said first chamber means includes one or more orifices as the means for varying the resistance of said first chamber means to the flow of air therethrough.

4. An apparatus for delivering aerosolized medication to a patient, of the type including a medication container and metering means, said apparatus comprising:
    a first rigid chamber;
    a second collapsible chamber;
    a mouthpiece, said mouthpiece having a first end and a second end, said mouthpiece having a first passageway extending lengthwise therethrough from said first end to said second end, said first end being shaped to accommodate the human mouth for inhalation purposes, said mouthpiece further having a second passageway transverse to said first passageway, said second passageway being positioned between said first end and said second end and being in open communication with said first passageway, said mouthpiece further including means for connecting to the medication container, and passage means for directing medication from the container out the second end of said mouthpiece for discharge into said first rigid chamber;
    said first rigid chamber having first and second end walls, said first end wall having an opening which is pneumatically connected to said first passageway of said mouthpiece at the second end thereof, the second end wall of said first rigid chamber having means for limiting the volumetric flow of air therethrough; and
    said second collapsible chamber being pneumatically connected to said second passageway in said mouthpiece;
    thereby allowing the patient to meter medication into said first rigid chamber, and to inhale through said mouthpiece, automatically inhaling the non-medicated contents of said second collapsible chamber before inhaling the medication from the rigid first chamber.

5. Apparatus according to claim 4, wherein the medication container comprises a pressurized aerosol.

6. Apparatus according to claim 4, wherein the medication container comprises a spray dispenser.

7. Apparatus according to claim 4, wherein said limiting means comprises means defining one or more orifices for limiting the volumetric flow of air through said first rigid chamber to 30 liters per minute or less.

8. Apparatus according to claim 4, wherein said second collapsible chamber has flexible walls, whereby the volume of gas held in said chamber is adjustable.

9. Apparatus according to claim 8, further comprising indicia on the outside of said collapsible chamber to indicate said adjustable volume.

10. A device for aiding a patient in inhaling medication, of the type having a pressurized aerosol medication container and having a metering means, said device comprising:
- a first rigid chamber;
- a second collapsible chamber, said second collapsible chamber including means for adjusting the volume of air contained therein and indicia means to indicate said adjustable volume;
- a mouthpiece, said mouthpiece having a near and far end, said mouthpiece having a first opening therethrough, said first opening connecting said near end to said far end, said near end being shaped to accommodate the human mouth, said mouthpiece further having a second opening between said near end and said far end, said second opening meeting said first opening, and said mouthpiece further including means for connecting said mouthpiece to the medication container, and means for directing the medication out the far end of said mouthpiece into said first rigid chamber;
- said first rigid chamber having a first and second end, said first end having an opening pneumatically connected to said far end of said mouthpiece;
- said first rigid chamber further including one or more small orifices in its second end for the purpose of limiting the volumetric flow of air therethrough so that the volumetric flow rate is at or below 30 liters per minute; and
- said second collapsible chamber being pneumatically connected to said second opening in said mouthpiece;
- thereby allowing the patient to first meter medication into said first rigid chamber, and to inhale through said mouthpiece, while automatically inhaling the non-medicated contents of said second collapsible chamber for inhaling medication through the rigid first chamber.

* * * * *